(12) United States Patent
Watson et al.

(10) Patent No.: US 8,254,023 B2
(45) Date of Patent: Aug. 28, 2012

(54) OPTICAL TOMOGRAPHY SYSTEM WITH HIGH-SPEED SCANNER

(75) Inventors: Mathew D. Watson, Bellevue, WA (US); Jon W. Hayenga, Redmond, WA (US)

(73) Assignee: Visiongate, Inc., Phoenix, AZ (US)

( * ) Notice: Subject to any disclaimer, the term of this patent is extended or adjusted under 35 U.S.C. 154(b) by 619 days.

(21) Appl. No.: 12/391,096

(22) Filed: Feb. 23, 2009

(65) Prior Publication Data
US 2010/0214639 A1    Aug. 26, 2010

(51) Int. Cl.
*G02B 23/14* (2006.01)
*G02B 21/00* (2006.01)

(52) U.S. Cl. .................... 359/432; 359/368; 359/380

(58) Field of Classification Search .......... 359/368–390, 359/432, 676
See application file for complete search history.

(56) References Cited

U.S. PATENT DOCUMENTS

| | | |
|---|---|---|
| 3,560,754 A | 2/1971 | Kamentsky |
| 3,598,471 A | 8/1971 | Baldwin |
| 3,657,537 A | 4/1972 | Wheeless, Jr. |
| 3,705,771 A | 12/1972 | Friedman et al. |
| 3,960,449 A | 6/1976 | Carlton |
| 3,999,047 A | 12/1976 | Green |
| 4,081,277 A | 3/1978 | Brault et al. |
| 4,110,043 A | 8/1978 | Eisert |
| 4,175,860 A | 11/1979 | Bacus |
| 4,183,623 A | 1/1980 | Haines |
| 4,293,221 A | 10/1981 | Kay |
| 4,360,885 A | 11/1982 | Edgar |
| 4,702,598 A | 10/1987 | Bohmer |
| 4,786,165 A | 11/1988 | Yamamoto |
| 4,858,128 A | 8/1989 | Nowak |
| 4,873,653 A | 10/1989 | Grosskopf |
| 5,034,613 A | 7/1991 | Denk |
| 5,117,466 A | 5/1992 | Buican |
| 5,125,737 A | 6/1992 | Rodriguez et al. |
| 5,141,609 A | 8/1992 | Sweedler |
| 5,148,502 A | 9/1992 | Tsujiuchi |
| 5,159,398 A | 10/1992 | Maekawa et al. |
| 5,189,518 A | 2/1993 | Nishida et al. |
| 5,281,517 A | 1/1994 | Bacus |

(Continued)

FOREIGN PATENT DOCUMENTS

WO   WO2006611885 A2   9/2006

OTHER PUBLICATIONS

Schmitz et al., "Performance Characteristics of a Silicon Photodiode (SiPD) Based Instrument for Fast Functional Optical Tomography," SUNY Downstate Medical Center, Brooklyn, NY 11203 (2001).

(Continued)

*Primary Examiner* — Thong Nguyen
(74) *Attorney, Agent, or Firm* — George A. Leone; Citadel Patent Law (57) ABSTRACT

An object of interest is illuminated within the field of view of a microscope objective lens located to receive light passing through the object of interest. Light transmitted through the microscope objective lens impinges upon a variable power element. The variable power element is driven with respect to the microscope objective lens to scan through multiple focal planes in the object of interest. Light transmitted from the variable power element is sensed by a sensing element or array.

30 Claims, 7 Drawing Sheets

U.S. PATENT DOCUMENTS

| | | | |
|---|---|---|---|
| 5,308,990 | A | 5/1994 | Takahashi |
| 5,312,535 | A | 5/1994 | Waska et al. |
| 5,321,501 | A | 6/1994 | Swanson |
| 5,333,164 | A | 7/1994 | Tam |
| 5,390,226 | A | 2/1995 | Tam |
| 5,402,460 | A | 3/1995 | Johnson |
| 5,428,447 | A * | 6/1995 | Toida ............................ 356/601 |
| 5,539,800 | A | 7/1996 | Katsevich |
| 5,548,395 | A | 8/1996 | Kosaka |
| 5,552,605 | A | 9/1996 | Arata |
| 5,644,388 | A | 7/1997 | Maekawa et al. |
| 5,680,484 | A | 10/1997 | Ohyama |
| 5,710,429 | A | 1/1998 | Alfano |
| 5,741,411 | A | 4/1998 | Yeung |
| 5,760,901 | A | 6/1998 | Hill |
| 5,760,951 | A | 6/1998 | Dixon |
| 5,786,893 | A * | 7/1998 | Fink et al. ..................... 356/301 |
| 5,831,723 | A | 11/1998 | Kubota |
| 5,835,617 | A | 11/1998 | Ohta et al. |
| 5,880,838 | A | 3/1999 | Marx et al. |
| 5,915,048 | A | 6/1999 | Hill et al. |
| 6,005,617 | A | 12/1999 | Shimamoto et al. |
| 6,026,174 | A | 2/2000 | Palcic |
| 6,038,067 | A | 3/2000 | George |
| 6,072,624 | A | 6/2000 | Dixon et al. |
| 6,078,681 | A | 6/2000 | Silver |
| 6,091,983 | A | 7/2000 | Alfano et al. |
| 6,130,958 | A | 10/2000 | Rohler et al. |
| 6,177,277 | B1 | 1/2001 | Soini |
| 6,201,628 | B1 | 3/2001 | Basiji |
| 6,211,955 | B1 | 4/2001 | Basiji |
| 6,215,587 | B1 | 4/2001 | Alfano et al. |
| 6,239,871 | B1 | 5/2001 | Gilby |
| 6,248,988 | B1 | 6/2001 | Kranz |
| 6,249,341 | B1 | 6/2001 | Basiji et al. |
| 6,251,586 | B1 | 6/2001 | Mulshine |
| 6,251,615 | B1 | 6/2001 | Oberhardt |
| 6,256,096 | B1 | 7/2001 | Johnson |
| 6,291,824 | B1 | 9/2001 | Battarbee |
| 6,312,914 | B1 | 11/2001 | Kardos et al. |
| 6,365,367 | B1 | 4/2002 | Friedman et al. |
| 6,374,128 | B1 * | 4/2002 | Toida et al. ................... 600/310 |
| 6,388,809 | B1 | 5/2002 | Macaulay |
| 6,473,176 | B2 | 10/2002 | Basiji |
| 6,519,355 | B2 | 2/2003 | Nelson |
| 6,522,775 | B2 | 2/2003 | Nelson et al. |
| 6,529,614 | B1 | 3/2003 | Chao |
| 6,540,895 | B1 | 4/2003 | Spence |
| 6,591,003 | B2 | 7/2003 | Chu et al. |
| 6,608,682 | B2 | 8/2003 | Ortyn et al. |
| 6,624,930 | B1 | 9/2003 | Danner et al. |
| 6,636,623 | B2 | 10/2003 | Nelson et al. |
| 6,640,014 | B1 | 10/2003 | Price |
| 6,697,508 | B2 | 2/2004 | Nelson |
| 6,741,730 | B2 | 5/2004 | Rahn et al. |
| 6,770,893 | B2 | 8/2004 | Nelson |
| 6,775,399 | B1 | 8/2004 | Jiang |
| 6,842,297 | B2 | 1/2005 | Dowski, Jr. |
| 6,850,587 | B1 | 2/2005 | Karimi |
| 6,868,177 | B1 | 3/2005 | Camahort |
| 6,944,322 | B2 | 9/2005 | Johnson et al. |
| 6,975,400 | B2 | 12/2005 | Ortyn et al. |
| 6,985,232 | B2 * | 1/2006 | Sezginer ....................... 356/451 |
| 6,991,738 | B1 | 1/2006 | Fauver |
| 7,003,143 | B1 | 2/2006 | Hewitt |
| 7,050,087 | B2 | 5/2006 | Harari |
| 7,075,647 | B2 | 7/2006 | Christodoulou |
| 7,141,773 | B2 | 11/2006 | Kaplan et al. |
| 7,197,355 | B2 | 3/2007 | Nelson |
| 7,218,393 | B2 | 5/2007 | Sharpe et al. |
| 7,224,540 | B2 | 5/2007 | Olmstead et al. |
| 7,260,253 | B2 | 8/2007 | Rahn et al. |
| 7,274,809 | B2 | 9/2007 | Macaulay et al. |
| 2001/0012069 | A1 | 8/2001 | Derndinger et al. |
| 2002/0122167 | A1 | 9/2002 | Riley et al. |
| 2003/0063384 | A1 | 4/2003 | Dowski, Jr. |
| 2003/0199758 | A1 | 10/2003 | Nelson |
| 2003/0222197 | A1 | 12/2003 | Reese |
| 2004/0001618 | A1 | 1/2004 | Johnson |
| 2004/0008515 | A1 | 1/2004 | Brown |
| 2004/0036875 | A1 | 2/2004 | Kramer |
| 2004/0076319 | A1 | 4/2004 | Fauver et al. |
| 2004/0197839 | A1 | 10/2004 | Daniely et al. |
| 2004/0217256 | A1 | 11/2004 | Ortyn et al. |
| 2004/0228520 | A1 | 11/2004 | Dresser |
| 2005/0006595 | A1 | 1/2005 | Goodwin et al. |
| 2005/0085708 | A1 | 4/2005 | Fauver et al. |
| 2005/0085721 | A1 | 4/2005 | Fauver et al. |
| 2005/0248837 | A1 * | 11/2005 | Sase et al. ..................... 359/380 |
| 2006/0023219 | A1 | 2/2006 | Meyer et al. |
| 2006/0066837 | A1 | 3/2006 | Ortyn et al. |
| 2006/0068371 | A1 | 3/2006 | Ortyn et al. |
| 2006/0093200 | A1 | 5/2006 | Sharpe et al. |
| 2006/0096358 | A1 | 5/2006 | Fauver et al. |
| 2006/0099707 | A1 | 5/2006 | Nelson et al. |
| 2006/0171041 | A1 | 8/2006 | Olmstead et al. |
| 2006/0183220 | A1 | 8/2006 | Nelson et al. |
| 2006/0188869 | A1 | 8/2006 | Zeskind et al. |
| 2006/0204071 | A1 | 9/2006 | Ortyn et al. |
| 2007/0071357 | A1 | 3/2007 | Rahn et al. |
| 2007/0146873 | A1 | 6/2007 | Ortyn et al. |
| 2007/0215528 | A1 | 9/2007 | Hayenga et al. |
| 2007/0258122 | A1 | 11/2007 | Chamgoulov et al. |

OTHER PUBLICATIONS

Schmizt et al., "Instrument for Real-Time Dynamic Optical Tomography," SUNY Downstate Medical Center, Brooklyn, NY 11203 (2002).

King, M.C. and Berry, D.H., "A Depth Scanning Microscope," Applied Optics, vol. 10, No. 1, Jan. 1971 pp. 208-210.

Shannon, "The Art and Science of Optical Design," (1977) University of Arizona, Cambridge University Press, Fig. 4.12 and Fig. 4.13.

Anderson, RH, "Close-up imaging of documents and displays with lens arrays," AppliedOptics (1979) 18, 477.

Dziedzic-Goclawska, et al., "Application of the Optical Fourier Transform for Analysis of the Spatial Distribution of Collagen Fibers in Normal and Osteopetrotic Bone Tissue," Histochemistry (1982) 74:123-137.

Pieper, R.J. and Korpel A., "Image processing for extended depth of field, Applied Optics," vol. 22, No. 10, May 15, 1983, pp. 1449-1453.

Reymond et al., "A Routine Flat Embedding Method for Electron Microscopy of Microorganisms Allowing Selection and Precisely Orientated Sectioning of Single Cells by Light Microscopy," Journal of Microscopy, vol. 130 Pt. 1 Apr. 1983 pp. 79-84.

Ong, S. H., "Development of an imaging flow cytometer." Anal Quant Cytol Histol (1987) 9(5)pp. 375-382.

Steward, E. G., Fourier Optics: An Introduction, 2nd ed. (Halsted Press, New York) 1987.

Kak, A.C. and Slaney, M., Principles of Computerized Tomographic Imaging, IEEE Press, (New York) 1988.

Press, W.H. et al., Numerical Recipes in C (New York: Cambridge University Press) 1988.

Kinney, J. H., "Energy-modulated X-ray Microtomography", Rev. Sci. Instrum. 1988, 59(1)pp. 196-197.

Manglos, S. H. et al., "Maximum Likelihood Reconstruction for Cone Beam SPECT: Development and Initial Tests," Physics in Medicine and Biology, 1989, 34(12)pp. 1947-1957, #1382.

Singer, J. R. et al., "Image Reconstruction of the Interior of Bodies that Diffuse Radiation," Science, 1990, 248(4958) pp. 990-993.

Kinney, J. H., "X-ray Tomographic Microscopy (XTM) Using Synchrotron Ratiation", Annu. Rev. Mater. Sci., 1992, 22pp. 121-152.

Cheng, P. C., "Review on the Development of Cone-beam X-ray Microtomography, Proceedings of the X-ray Optics and Microanalysis," Institute of Physics Ser. No. 130, Kenway, PB, et al. (eds.), Manchester, UK, Aug. 31-Sep. 4, 1992 pp. 559-566.

Kikuchi, S., "Three-dimensional computed tomography for optical microscopes," Optics Communications (1994) 107, 432-444.

Tiziani, H. J. et al., "Three-dimensional analysis by a microlens array confocal arrangements," Applied Optics (1994) 33, 567.

Paulsen, K. D., "Spatially Varying Optical Property Reconstruction Using a Finite Element Diffusion Equation Approximation," Medical Physics (1995) 22(691-701).

Shapiro, H. M., Practical Flow Cytometry, 1995, 3rd ed., Wiley-Liss.

Pawley, J. B., Handbook of Biological Confocal Microscopy, (1995) Plenum Press, NY 479-490.

Wedberg, T.C., "Recent results in optical diffraction microtomography," Meas. Sci. Technol., 1996, vol. 7, p. 414.

Kikuchi, S. et al., "Three-dimensional microscope computed tomography based on general Radon transform for optical imaging systems," Optics Communications 123 (1996) 725-733.

Bradburn S. et al., "Realizations of Focus Invariance in Optical/Digital Systems with Wavefront Coding," Applied Optics, 1997, vol. 36, Issue 35, pp. 9157-9166.

Preza, C. et al., "Three-Dimensional Transmitted-Light DIC Microscopy," Presented at SPIE's BiOS97; 3D Microscopy: Image Acquisition and Processing IV, 2984-24, 1997.

Sheppard, C. J. R. & Torok, P., "Effects of specimen refractive index on confocal imaging," Journal of Microscopy, vol. 185, Pt. 3, Mar. 1997, pp. 366-374.

Jorgensen, S. M., "Three Dimensional Imaging of Vasculature and Parenchyma in Intact Rodent Organs with X-ray Micro-CT", Am. J. Physiology 275, 1998, (Heart Circ. Physiol. 44) pp. H1103-H1114.

Taguchi, K. and Aradate, H., "Algorithm for Image Reconstruction in Multi-slice Helical CT", Medical Physics 25 (4) (1998) pp. 550-561.

Hampel, U. and Freyer, R., "Fast Image Reconstruction for Optical Absorption Tomography in Media with Radially Symmetric Boundaries," Medical Physics 25 (1) (1998) pp. 92-101.

Zhang, J. et al., "Membrane Electric Properties by Combined Patch Clamp and Fluorescence Ratio Imaging in Single Neurons," Biophysical Journal vol. 74 Jan. 1998 48-53.

Tucker, S.C. et al., "Extended depth of field and aberration control for inexpensive digital microscope systems," Optics Express, vol. 4, No. 11, May 24, 1999, pp. 467-474.

Edelmann, P. et al., "Correlation of chromatic shifts and focal depth in Spectral Precision Distance Microscopy measured by Micro Axial Tomography," Optical Biopsies and Microscopic Techniques III, Sep. 1999, SPIE vol. 3568, pp. 89-95.

Marks D. L. et al., Three-dimensional tomography using a cubic-phase plate extended depth-of-field system, Optics Letters, Feb. 15, 1999, vol. 24, No. 4.

George, J.S. et al., Virtual Pinhole Confocal Microscope, Physics Division Progress Report, 1999-2000, www.lanl.gov/p/pdfs/papp_pinhole.pdf.

Defrise, M. et al., "A Solution to the Long-object Problem in Helical Cone-beam Tomography," Physics in Medicine and Biology, 2000, 45(623-43).

Sanyal, S. and Ghosh, A., "High focal depth with a quasi-bifocus birefringent lens, Applied Optics," vol. 39, No. 14, May 10, 2000 pp. 2321-2325.

Mueller, K. and Yage, R., Rapid 3-D Cone-beam Reconstruction with the Simultaneous Algebraic Reconstruction Technique (SART) Using 2-D Texture Mapping Hardware, IEEE Transactions on Medical imaging, 2000, 19(12) pp. 1227-1237.

Endo, M. et al., "Effect of Scattered Radiation on Image Noise in Cone Beam CT," Medical Physics, 2001, 28(4) (469-74).

Herzenberg, L. A., The History and Future of the Fluoresence Activated Cell Sorter and Flow Cytometry: A View from Stanford, (2002).

Sharpe, J. et al., "Optical Projection Tomography as a Tool for 3D Microscopy and Gene Expression Studies," Science, vol. 296, pp. 541-545, Apr. 19, 2002.

Xu, Y. et al., "Three-dimensional diffuse optical tomography of bones and joints," J. Biomed. Optics, vol. 7, (2002), p. 88.

Widjanarko, T., et al., "A post-processing technique for extending depth of focus in conventional optical microscopy," Optics & Laser Technology, 2002, 34, pp. 299-305.

Bentley, M. D., "The Use of Microcomputed Tomography to Study Microvasculature in Small Rodents," American Journal of Physiology (Regulatory Integrative Comp Physiol), 2002, 282(R1267-R1279).

Martini, N. et al., "A new high-aperture glycerol immersion objective lens and its application to 3D-fluoresence microscopy," Journal of Microscopy vol. 206 Pt. 2, May 2002, pp. 146-151.

Polymicro Technologies "Square Flexible Fused Silica Capillary Tubing," (2003) www.polymicro.com.

Matula, P. et al., "Precise 3D image alignment in micro-axial tomography," Journal of Microscopy, vol. 209, Pt. 2 (Feb. 2003) pp. 126-142.

Sharpe, J. et al., Review, "Optical Projection Tomography as a New Tool for Studying Embryo Anatomy," J. Anat. (2003), pp. 175-181.

Lane, P.M. et al., Confocal Microendoscopy with Chromatic Sectioning, Spectral Imaging: Instrumentation, Applications, and Analysis II, Proc. of SPIE (2003) vol. 4959 pp. 23-26.

Fauver et al., Development of Micro-Optical Projection Tomography for 3D Analysis of Single Cells, Image Acquisition and Processing XI. Edited by Conchello, Jose-Angel; Cogswell, Carol J.; Wilson, Tony. Proceedings of the SPIE (2004), vol. 5324, pp. 171-181.

Porras, R. et al., Wavefront coding technology in the optical design of astronomical instruments, 5th Iberoamerican Meeting on Optics and 8th Latin American Meeting on Optics, Lasers, and Their Applications, edited by A. Marcano O., J. L. Paz, Proc. of SPIE (2004) vol. 5622, pp. 796-800.

Forster, B. et al., "Complex Wavelets for Extended Depth-of-Field: A New Method for the Fusion of Multichannel Microscopy Images," Microscopy Research and Technique, 2004, 65:33-42.

Gao X., et al., "Tunable focal depth of an apodized focusing optical system," Optical Engineering 44(6), 063001, 1-9, (Jun. 2005).

Fauver et al., Three-dimensional imaging of single isolated cell nuclei using optical projection tomography, Optics Exress, May 30, 2005/vol. 13 No. 11/4210-4223.

Miks, A. et al., "Theory of hyperchromats with linear longitudinal chromatic, aberration," Proc. of SPIE, 2005, vol. 5945, pp. 59450, Y1-Y8.

Abragamsson, S. et al., A new approach to extended focus for high-speed, high-resolution biological microscopy, Proc. of SPIE (2006) vol. 60900, N1-N8.

Chang, et al., "Enhanced live cell membrane imaging using surface plasmon-enhanced total internal reflection fluorence microscopy," Optics Express 9308, vol. 14, No. 20, Oct. 2, 2006.

Curry A. et al., "Epi-illumination through the microscope objective applied to darkfield imaging and microspectroscopy of nanoparticle," Jul. 10, 2006, vol. 14, No. 14, Optics Express 6535.

Leitgeb, R. et al., "Extended focus depth for Fourier domain optical coherence microscopy," Optics Letters, Doc. ID 69650, Jun. 2006.

Somayaji, M. et al., "Enhancing form factor and light collection of multiplex imaging systems by using a cubic phase mask," Applied Optics, vol. 45, No. 13, May 2006, pp. 2911-2923.

Darrell, A., et al., "Accounting for Point Source Propagation Properties in 3D Fluorescence OPT," Proceedings of the 28th IEEE, EMBS Annual International Conference, New York City, USA, Aug. 30-Sep. 3, 2006.

Mikula, G. et al., "Imaging with extended focal depth by means of lenses with radial and angular modulation," Optics Express, vol. 15, No. 15, Jul. 23, 2007, pp. 9184-9193.

Kerfoot, et al., "Quantitative Multiplex Chromagenic Immunohistochemistry," Mosaic Laboratories, (2007) www.mosaiclabs.com, Tuscon Symposium.

Xu, Y. et al., "Ultra long high resolution beam by multi-zone rotationally symmetrical complex pupil filter," Optics Express, vol. 15, No. 10, May 10, 2007, pp. 6409-6413.

Long, J.C. et al., Tube Lens Focal Length, Nikon Microscopy U: Interactive Java Tutorials, (2007) http://www.microscopy.com.

Conchello, J-A. et al., "Extended depth-of-focus microscopy via constrained deconvolution," Journal of Biomedical Optics 12 (6), 064026 (Nov./Dec. 2007).

Zeskind, B.J., et al., Nucleic acid and protein mass mapping by live-cell deepultraviolet, Nature Methods, published online, 4, 567-569, Jun. 3, 2007; DOI:101038/NMETH1053.

Zeskind, B.J., Nucleic acid and protein mass mapping by live-cell deepultraviolet, Nature Methods, published online, 4, 567-569, Jun. 3, 2007; DOI:101038/NMETH1053 (Supplementary Figures and Text).

Berge, B. et al., "Liquid Lens Technology: Principle of Electrowetting Based Lenses and Applications to Imaging," Micro Electro Mechanical Systems, Jan. 30-Feb. 3, 2005. MEMS 2005. 18th IEEE International Conference on, p. 227-230.

Gabay, C. et al., "Dynamic Study of Varioptic variable focal lenses," Proc. SPIE, vol. 4767, 159 (2002); DOI:10.1117/12.468224.

Physik Instrumente, "P-725 PIFOC® Long-Travel Objective Scanner High-Precision Positioner / Scanner for Microscope Objectives," 2008, http://www.physikinstrumente.com/en/products/prdetail.php?sortnr=200375.

* cited by examiner

OPTICAL TOMOGRAPHY SYSTEM WITH HIGH-SPEED SCANNER

TECHNICAL FIELD

The present invention relates to optical tomographic imaging systems in general, and, more particularly, to a high-speed focal plane scanner for optical projection tomography, in which a small object, such as a biological cell, is imaged by a microscope.

BACKGROUND

Recently advances in imaging biological cells using optical tomography invented by A. C. Nelson have been disclosed, for example, in U.S. Pat. No. 6,522,775, issued Feb. 18, 2003, and entitled "Apparatus And Method For Imaging Small Objects In A Flow Stream Using Optical Tomography," the full disclosure of which is incorporated by reference. Further developments in the field are taught in Fauver et al., U.S. Pat. No. 7,738,945 issued on Jun. 15, 2010, entitled "Method And Apparatus Of Shadowgram Formation For Optical Tomography," and Fauver et al., U.S. Pat. No. 7,907,765, issued on Mar. 15, 2011, entitled "Focal Plane Tracking For Optical Microtomography," the full disclosures of which are also incorporated by reference.

Processing in such an optical tomography system begins with specimen preparation. Typically, specimens taken from a patient are received from a hospital or clinic and processed to remove non-diagnostic elements, fixed and then stained. Stained specimens are then mixed with an optical fluid, inserted into a micro-capillary tube and images of objects, such as cells, in the specimen are produced using an optical tomography system. The resultant images comprise a set of extended depth of field images from differing perspectives called "pseudo-projection images." The set of pseudo-projection images can be reconstructed using backprojection and filtering techniques to yield a 3D reconstruction of a cell of interest.

The 3D reconstruction then remains available for analysis in order to enable the quantification and the determination of the location of structures, molecules or molecular probes of interest. An object such as a biological cell may be labeled with a stain or tagged molecular probe, and the measured amount and location of this probe may yield important information about the disease state of the cell, including, but not limited to, various cancers such as lung, breast, prostate, cervical and ovarian cancers.

In one type of optical tomography system, as described in U.S. Pat. No. 7,738,945 and constructed by VisionGate, Inc., the depth of field of the imaging optics is extended by scanning an objective lens transverse to a capillary tube containing a specimen. A piezoelectric transducer (PZT) actuator moves the objective lens sinusoidally several times per second in order to scan a series of focal planes though a specimen. By using a PZT actuator to move the objective lens, a focal plane moving through the specimen has its speed limited by inertia inherent in moving the objective lens rapidly along the optical axis through the specimen. Because the objective lens is housed in a relatively massive assembly, the scan rate is typically, about 10 Hz with a theoretical upper limit of roughly 60 cycles per second. During each scan an image sensor acquires at least one pseudo-projection image. With well-synchronized rotation and objective scanning, an image can be acquired on the down-stroke as well as the up-stroke of the PZT actuator, allowing up to 120 images per second to be acquired. While this is a useful acquisition rate, it can be significantly improved through the apparatus, systems and methods disclosed herein.

BRIEF SUMMARY OF THE DISCLOSURE

An optical projection tomography system and method for imaging an object of interest. An object of interest is illuminated within the field of view of a microscope objective lens located to receive light passing through the object of interest. Light transmitted through the microscope objective lens impinges upon a variable power element. The variable power element is driven to scan through multiple focal planes in the object of interest. Light transmitted from the variable power element is sensed by a sensing element or array.

In the drawings, identical reference numbers identify similar elements or components. The sizes and relative positions of elements in the drawings are not necessarily drawn to scale. For example, the shapes of various elements and angles are not drawn to scale, and some of these elements are arbitrarily enlarged and positioned to improve drawing legibility. Further, the particular shapes of the elements as drawn, are not intended to convey any information regarding the actual shape of the particular elements, and have been solely selected for ease of recognition in the drawings.

DETAILED DESCRIPTION OF THE PREFERRED EMBODIMENTS

The following disclosure describes several embodiments and systems for imaging an object of interest. Several features of methods and systems in accordance with example embodiments of the invention are set forth and described in the Figures. It will be appreciated that methods and systems in accordance with other example embodiments of the invention can include additional procedures or features different than those shown in Figures. Example embodiments are described herein with respect to biological cells. However, it will be understood that these examples are for the purpose of illustrating the principals of the invention, and that the invention is not so limited.

Additionally, methods and systems in accordance with several example embodiments of the invention may not include all of the features shown in these Figures. Throughout the Figures, like reference numbers refer to similar or identical components or procedures.

Unless the context requires otherwise, throughout the specification and claims which follow, the word "comprise" and variations thereof, such as, "comprises" and "comprising" are to be construed in an open, inclusive sense that is as "including, but not limited to."

Reference throughout this specification to "one example" or "an example embodiment," "one embodiment," "an embodiment" or various combinations of these terms means that a particular feature, structure or characteristic described in connection with the embodiment is included in at least one embodiment of the present invention. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

Definitions

Generally as used herein the following terms have the following meanings when used within the context of optical microscopy processes. The following definitions are provided to promote understanding of the disclosure and are not to be considered limiting:

"Capillary tube" has its generally accepted meaning and is intended to include transparent microcapillary tubes and equivalent items with an inside diameter generally of 500 microns or less.

"Depth of field" is the length along the optical axis within which the focal plane may be shifted before an unacceptable image blur for a specified feature is produced.

"Object" means an individual cell, particle, item, thing or other entity.

"Pseudoprojection" includes a single image representing a sampled volume of extent larger than the native depth of field of the optics. One concept of a pseudoprojection is taught in U.S. Pat. No. 7,738,945.

"Specimen" means a complete product obtained from a single test or procedure from an individual patient (e.g., sputum submitted for analysis, a biopsy, or a nasal swab). A specimen may be composed of one or more objects. The result of the specimen diagnosis becomes part of the case diagnosis.

"Sample" means a finished cellular preparation that is ready for analysis, including all or part of an aliquot or specimen.

Figure 1:
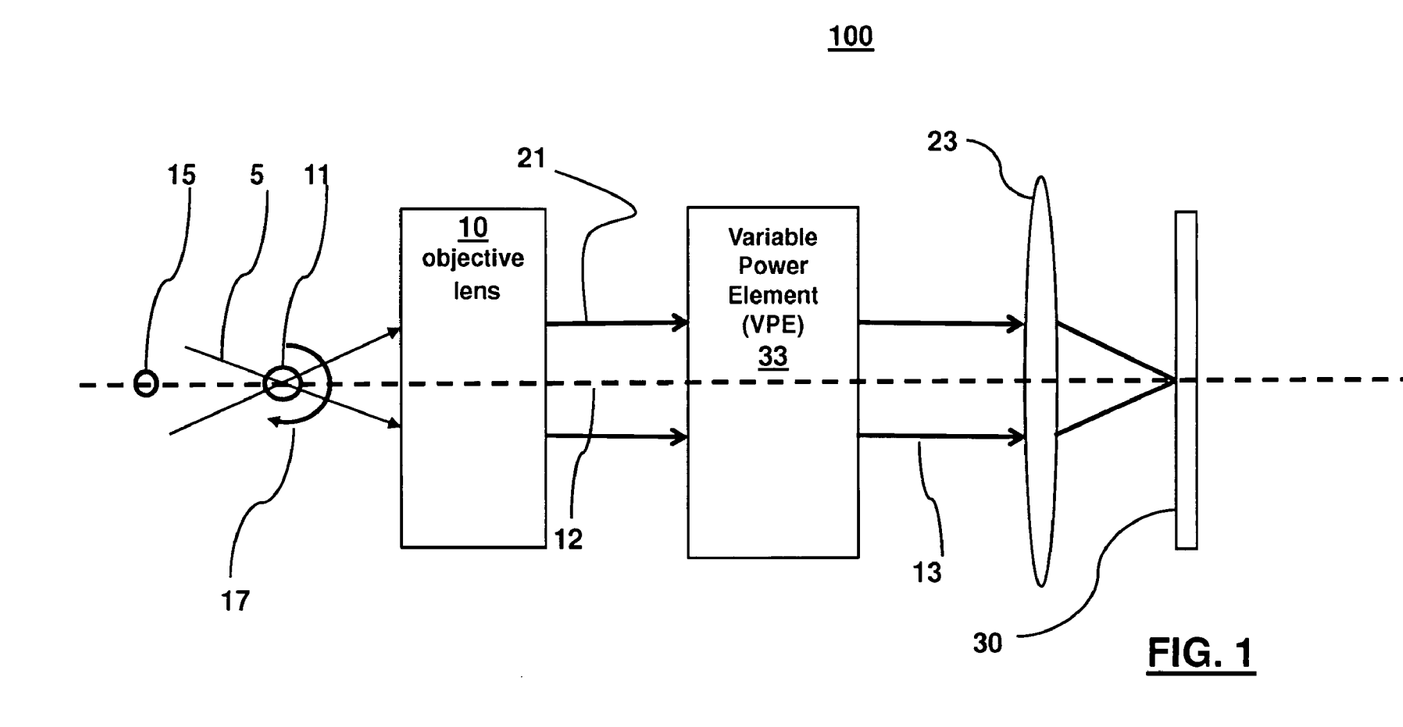
FIG. 1 schematically shows an example of a design for an optical tomography image acquisition system with a variable power element for high speed scanning.

Referring now to FIG. 1, an example of a design for an optical tomography image acquisition system with a variable power element for high speed scanning is schematically shown. An optical tomography system 100 includes an illuminator 15, a carrier 11, a variable power element 33, and a microscope objective assembly 10. A light sensor 30 is located in the focal plane of a tube lens 23 that, in turn, is located to receive light beams 13 transmitted from the variable power element 33. In an optical tomography system, for example, image signals acquired by the light sensor 30 are transmitted to a computer or like device for storage and image processing including 3D reconstruction.

In one embodiment, the illuminator 15 is located to illuminate a portion of carrier 11. The microscope objective assembly 10 is located to receive incident light 5 passing through the carrier 11 and objects residing in the carrier 11. The carrier 11 may be coupled to a rotational motor as signified by reference arrow 17. Under control of the rotational motor, the carrier 11 may be rotated to present various views of a transported object to the microscope objective assembly 10. The carrier 11 may advantageously comprise an optically transparent capillary tube or equivalent filled with an optical fluid selected for matching the refractive properties of the optics.

The variable power element 33 and microscope objective assembly 10 may be aligned along an optical path 12. Light 21 transmitted through the objective lens 10 impinges on the variable power element 33.

The light sensor 30 may advantageously comprise a photosensor array, a CCD array or equivalents. The illuminator 15 may comprise any suitable illumination source or combination of a plurality of illumination sources including sources producing visible light, near infrared, ultraviolet, and other light frequencies useful for optical tomography of fixed or live biological cells and equivalents.

Figure 2:
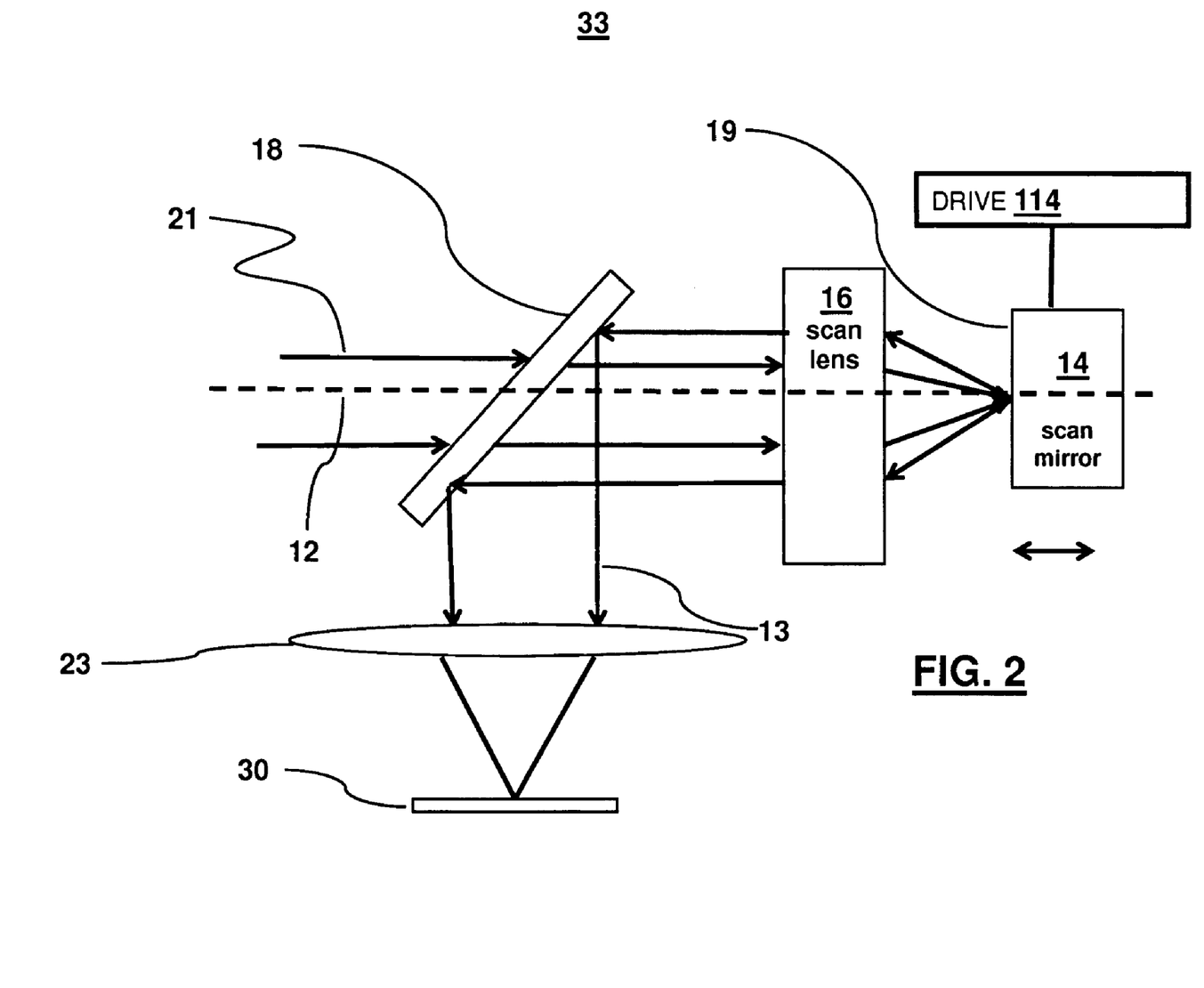
FIG. 2 schematically shows a more detailed example of a design for a variable power element and imaging optics.

Referring now to FIG. 2, a more detailed example of a design for a variable power element and imaging optics is schematically shown. A variable power element 33 includes a beamsplitter 18, a scan lens 16 and a scan mirror 14 having a reflecting surface 19. A light sensor 30 is located in the focal plane of a tube lens 23 that, in turn, is located to receive light beams 13 reflected from one surface of the beam splitter 18. The scan mirror 14 is coupled to be moved in a controlled manner by drive 114.

The beam splitter 18, scan lens 16 and scan mirror 14 are aligned along an optical path 12. The beam splitter 18 is also tilted at an angle for directing reflected light 13 from the scan mirror 14 through the tube lens 23, ultimately transmitted onto the light sensor 30 for acquiring images of the tube contents. Operating the scan mirror 14 comprises oscillating the scan mirror 14 along the optical axis while the reflecting surface 19 of the mirror maintains a substantially perpendicular relationship to the optical axis. As the scan mirror oscillates along the optical axis 12, a plurality of focal planes in the carrier 11 (shown in FIG. 1) are traversed and the resultant pseudo-projection is imaged on the light sensor 30.

Figure 3:
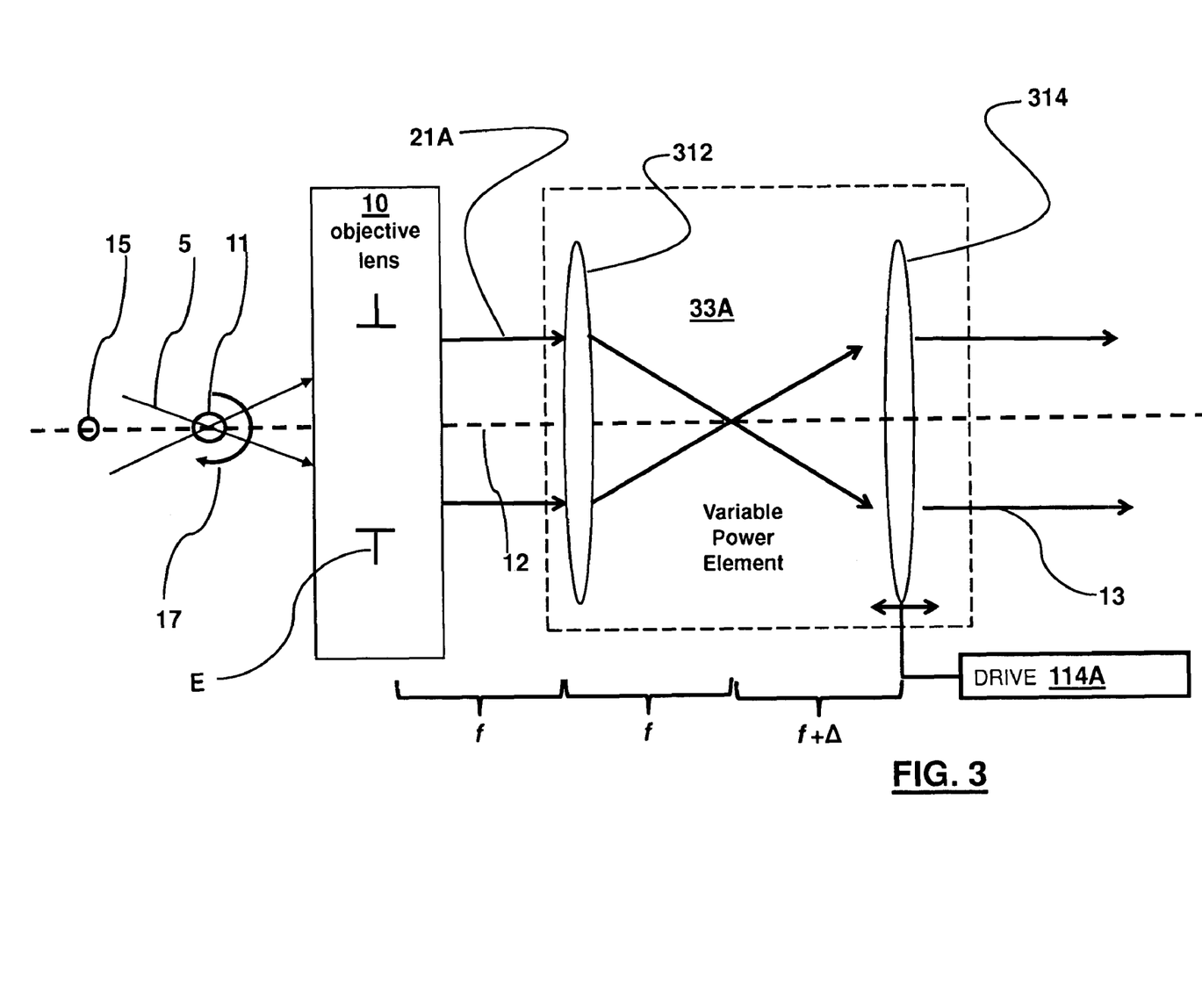
FIG. 3 schematically shows another example of a design for an optical tomography image acquisition system with a variable power element for high speed scanning.

Referring now to FIG. 3, another example of a design for an optical tomography image acquisition system with a variable power element for high speed scanning is schematically shown. An illuminator 15, a carrier 11, a variable power element 33A, and a microscope objective assembly 10 are aligned along an optical path 12, where the optical path 12 may be the optical axis of the microscope objective assembly 10. The microscope objective assembly 10 includes an exit pupil E. The variable power element 33A includes a first lens 312 and a second lens 314. The second lens 314 may advantageously comprise a scanning lens that is driven along the optical axis 12 by drive 114A. The exit pupil E, first lens 312 and second lens 314 are each separated by a focal length f. Movement of the second lens 314 operates to translate the second lens by a scanning distance $\Delta$ to scan focal plans in the carrier 11. In this example, the scanning distance $\Delta$ will oscillate between a positive and negative value represented here as f+$\Delta$.

Figure 4:
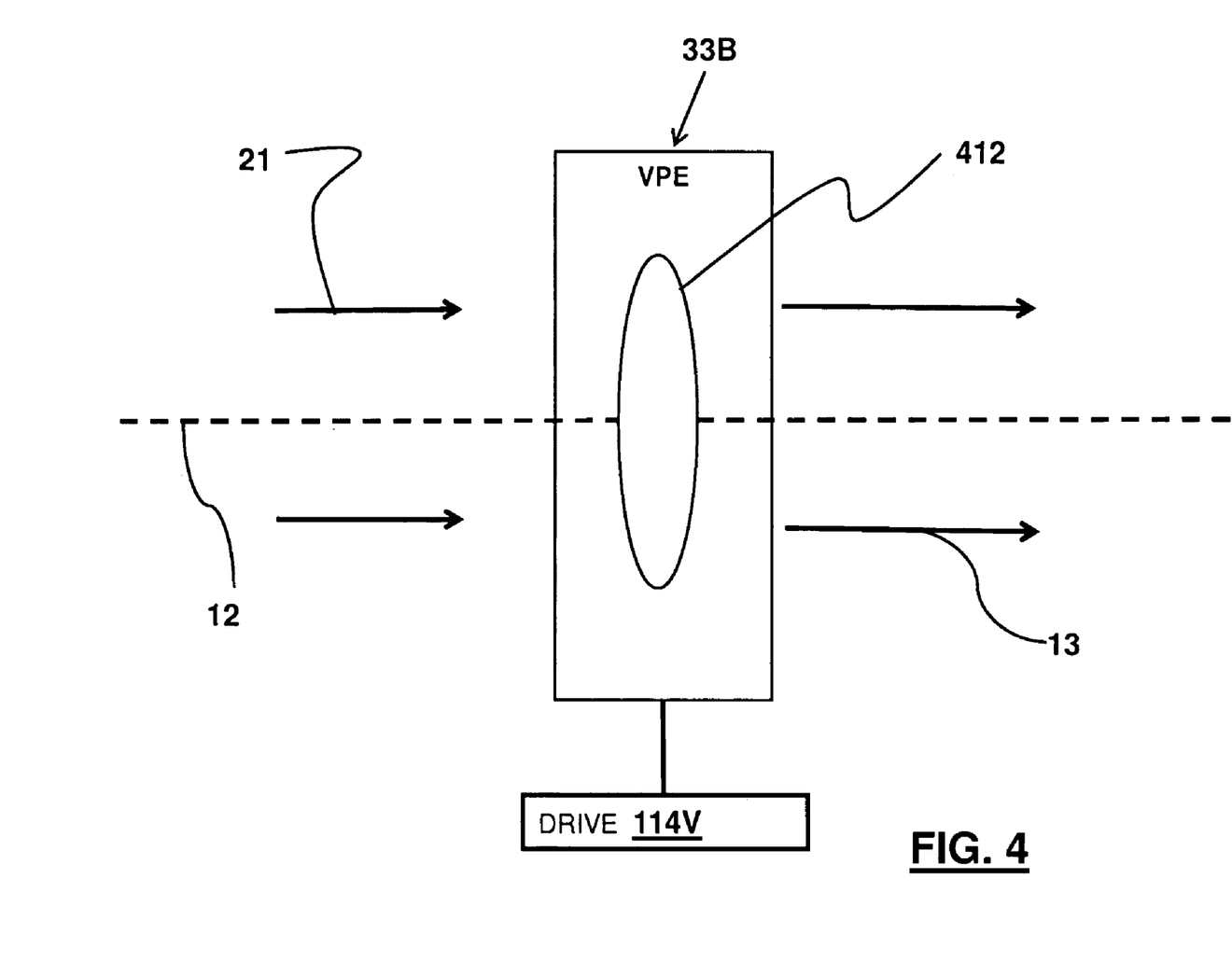
FIG. 4 schematically shows another example of a design for a variable power element.

Referring now to FIG. 4, another example of a design for a variable power element is schematically shown. The variable power element 33B includes a variable focal lens 412. In one embodiment, the variable focal lens 412 may be comprised of a transparent cell filled with two non-miscible fluids made according to "Varioptic" technology. Such Varioptic lenses are based on an electrowetting principle and are controllable using a variable voltage source 114V. Varioptic lenses are commercially available from Varioptic SA, Lyon, France. Such lenses can present large optical power variations. For example, a 5 mm diameter Varioptic lens can have an inverse focal length that varies up to 50 dioptries. (See, e.g., Gabay, et al. "Dynamic Study of a Varioptic variable focal lens," Current Developments in Lens Design and Optical Engineering III, Proceeding of SPIE Vol. 4767 (2002)).

Figure 5:
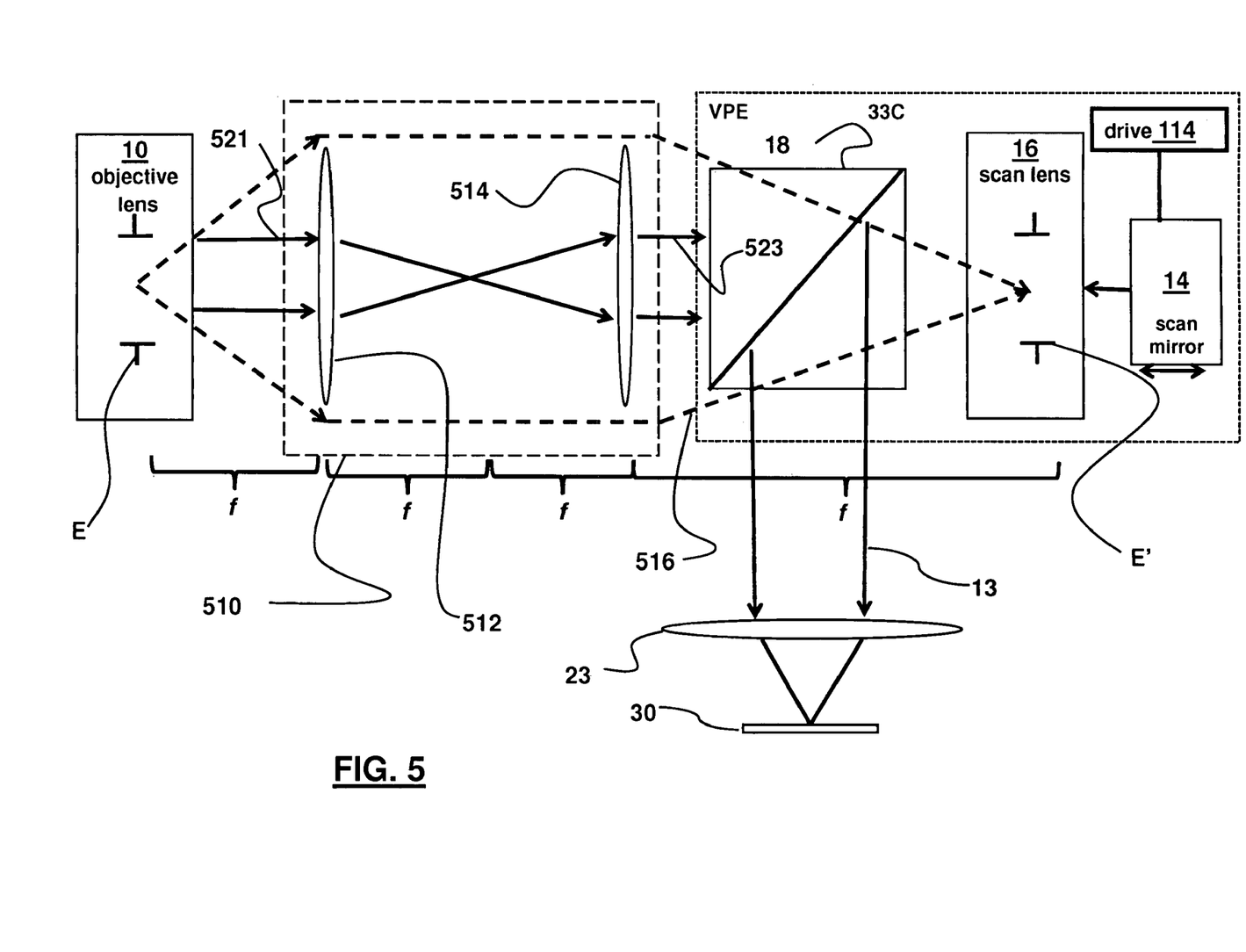
FIG. 5 schematically shows another example of a design for an optical tomography image acquisition system with a variable power element and optical relay.

Referring now to FIG. 5, another example of a design for an optical tomography image acquisition system with a variable power element and optical relay is schematically shown. A microscope objective assembly 10, an optical relay 510 and a variable power element 33C are aligned along an optical path. The microscope objective assembly 10 includes an exit pupil E. In one example, the variable power element 33C may include a beamsplitter 18 and a scan lens 16. The optical elements are each separated by a focal length f. E' represents the entrance pupil of the scan lens 16 which is coincident with the entrance pupil of the variable power element 33C. The broken line 516 indicates the light path for focusing the exit pupil E to be coincident with the entrance pupil E'. Light rays 521 represent light transmitted through the objective lens 10. Light rays 523 represent light relayed by optical relay 510.

The beam splitter 18 is configured for directing reflected light 13 from the scan lens 16 and scan mirror 14 through the tube lens 23, ultimately transmitted onto the light sensor 30 for acquiring images of the tube contents. The optical relay 510 includes a first focal lens 512 aligned with a second lens 514, where the first and second lenses are spaced by a distance of twice the focal length, 2f.

Having described the structure of example embodiments, a description of the operation of example embodiments should prove helpful to further understanding of the principles of the disclosure. Translating the scan mirror 14 a distance $\Delta z'$ produces a focus shift $\Delta z$ at the object equal to $2 \Delta z' n/(n' m_T^2)$, where n is the object space index of refraction, n' is the scanner space index of refraction, $m_T$ is the transverse magnification between the object and scanner. The factor of 2 is due to the fact that the optical path length changes by twice the mirror translation. Thus, by choosing an advantageous magnification ratio between the imaging objective and the scanning objective, focus can be translated using the scanning mirror with significantly less motion than would be required by moving the objective relative to the object. For example, a 50× objective lens 10 and a 100× scan lens 16 (i.e. transverse magnification $m_T$=0.5) yields an 8:1 reduction in scan distance required to generate a pseudo-projection, as compared to directly scanning the objective lens 10. Continuing this example, to create a 12 micron pseudo projection, the mirror need be scanned by only 1.5 microns.

The scan mirror need only be as large as the scanner space field of view, which is typically less than 1 mm. Thus a scan mirror 14 having a 1 mm diameter would be sufficient to reflect the entire image. Such a mirror weighs much less than a typical objective lens, and scanning such a mirror takes much less force and energy than does scanning the objective lens. The lower required force and shorter scan distance allow scan frequencies that are thousands of times greater than are feasible with a scanning objective. The scan mirror oscillates at a rate of at least 500 Hz and may also oscillate at a rate of at least 1000 Hz.

The scan mirror 14 and drive 114 may be made from a wide variety of available fabrication technologies. One example is a conventional first surface mirror attached to a piezoelectric actuator. Another example is a micro-electro-mechanical-systems (MEMS) flexure with a reflective coating. Yet another example is a metal mirror with a solenoid actuator. An acoustic wave generator driving a reflective elastic diaphragm may also be used. One skilled in the art will recognize that many other combinations of conventional actuators and reflectors may also be used.

The scan magnification $\Delta z/\Delta z'$ is independent of the numerical aperture (NA) of either the objective lens 10 or scan lens 16, but the NAs of the two lenses are indirectly tied to the scan magnification. Specifically, the entrance pupil E', of the scan lens 16 must be large enough to avoid vignetting in order to realize the resolving power of the objective lens 10 over the entire field of view. A consequence of this condition is that the scan lens 16 NA be equal to or larger than the objective lens 10 NA divided by the transverse magnification $m_T$, as follows from the optical invariant. The factor $m_T$ ties the NAs to the scan magnification $\Delta z/\Delta z'$. Equality is sufficient when the exit pupil E of the objective lens 10, or its image, is coincident with the entrance pupil E' of the scan lens 16, otherwise the scan lens 16 NA must be larger.

An optical relay may be used to image the exit pupil E of objective 10 onto the entrance pupil E' of scan lens 16. This is necessary if the lens pupils are virtual pupils, as is the case with most high performance high magnification microscope objectives. Moreover, a relay magnification $m_E$ of less than one, may be used to reduce the size of the image of the exit pupil of objective lens 10 to the point where it is the same size as the entrance pupil of scan lens 16. Using this technique has the side effect of also reducing the scan magnification by $m_E$.

The image magnification must remain constant while scanning to obtain a good pseudoprojection image. This is accomplished by making the system telecentric in scanner space. If the scan lens 16 is a telecentric lens, wherein its entrance pupil lies in its front focal plane, then the system will be telecentric in scanner space if and only if the exit pupil of objective lens 10, or its image, is coincident with its entrance pupil. If the scan lens 16 is not telecentric, then placing the exit pupil of objective lens 10, or its image, at the front focal plane of the scan lens 16 will make the system telecentric in scanner space, so long as the objective lens 10 exit pupil is not vignetted by scan lens 16. Once again, a relay system, as described in the previous paragraph, may be used to keep the magnification constant while scanning if either of the pupils is a virtual pupil.

If larger objects are scanned with lower objective lens 10 magnification, there is no need to change the scanning lens or translation distance $\Delta z'$. For example if a 20× lens is used for another application, the objective magnification ratio is 5:1 (i.e. transverse magnification $m_T$=0.2) yielding a 50:1 scan ratio. Thus a 1 micron translation of the position of the scan mirror produces a 50 micron shift in focal position of the image under the 20× lens. This allows scanning large ranges with micron or submicron motion. This is ideal for piezoelectric devices which are very precise. Such precision piezoelectric devices having motion characteristics of about 4 nm/volt motion, but with travel limited to about 10 microns, are commercially available.

Given the principles described, and assuming high performance microscope objectives with virtual pupils are used for objective lens 10 and scan lens 16, one advantageous embodiment includes (1) A scan lens having as high an NA as possible,
(2) A relay system to image the objective lens exit pupil onto the scan lens entrance pupil, and
(3) An objective lens whose NA matches the scan lens NA divided by the transverse magnification $m_T$.

Figure 6:
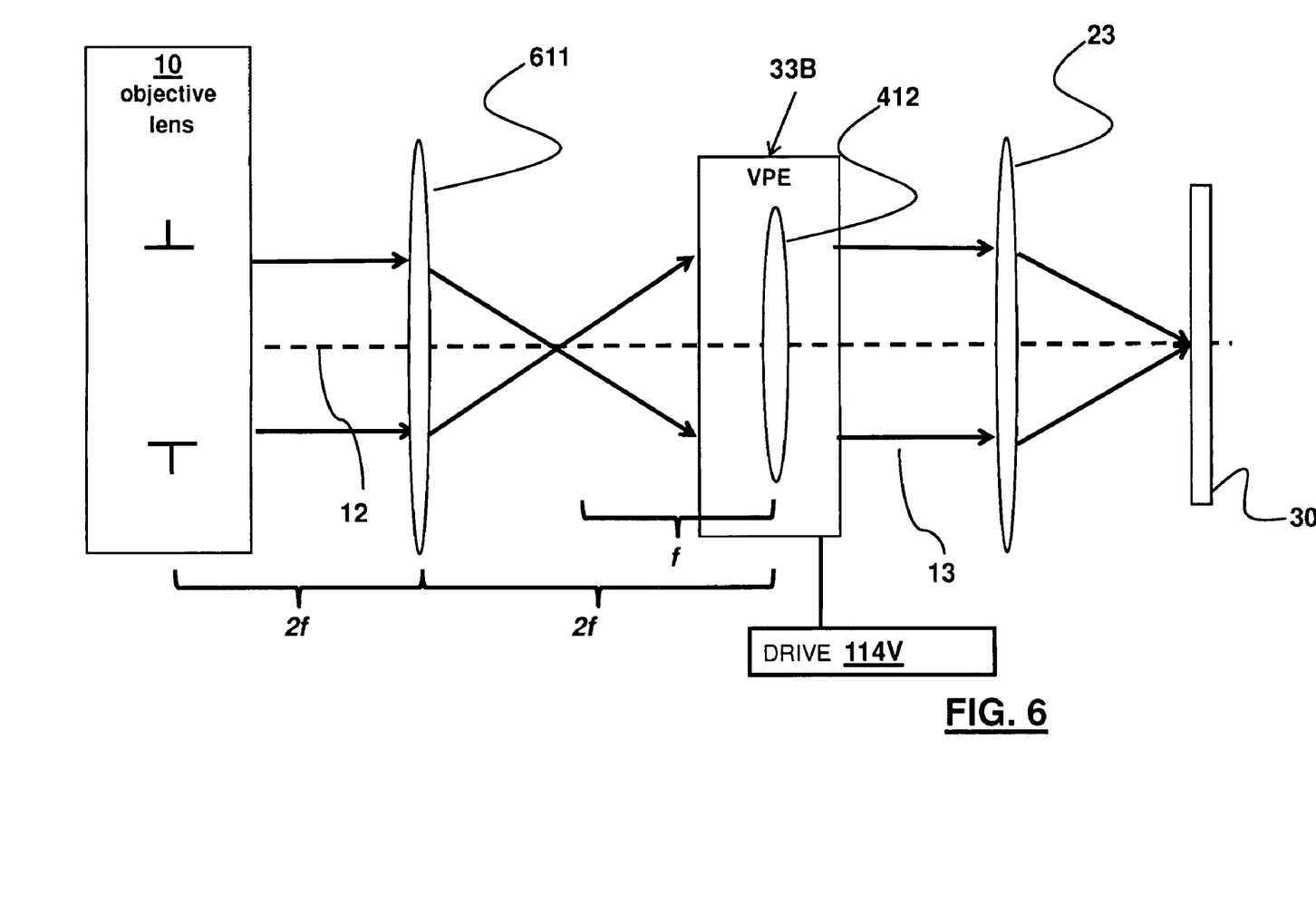
FIG. 6 schematically shows an alternate example of a design for an optical tomography image acquisition system with a liquid lens variable power element.

Referring now to FIG. 6, an alternate example of a design for an optical tomography image acquisition system with a liquid lens variable power element is schematically shown. A microscope objective assembly 10, a variable power element 33B are aligned along an optical path. The variable power element 33B includes a variable focal lens 412, for example a Varioptic lens or equivalent, as discussed above with reference to FIG. 4. An intermediate lens 611 is located in the optical path between the microscope objective assembly 10 and the variable power element 33B. The tube lens 23 is located to receive light beams 13 transmitted from the variable power element 33B and transmit the light beams to the light sensor 30. In one example, the variable focal lens 412 may be located a distance 2f from the intermediate lens 611. The intermediate lens 611 may advantageously be located at a distance 2f from the microscope objective assembly 10.

Figure 7:
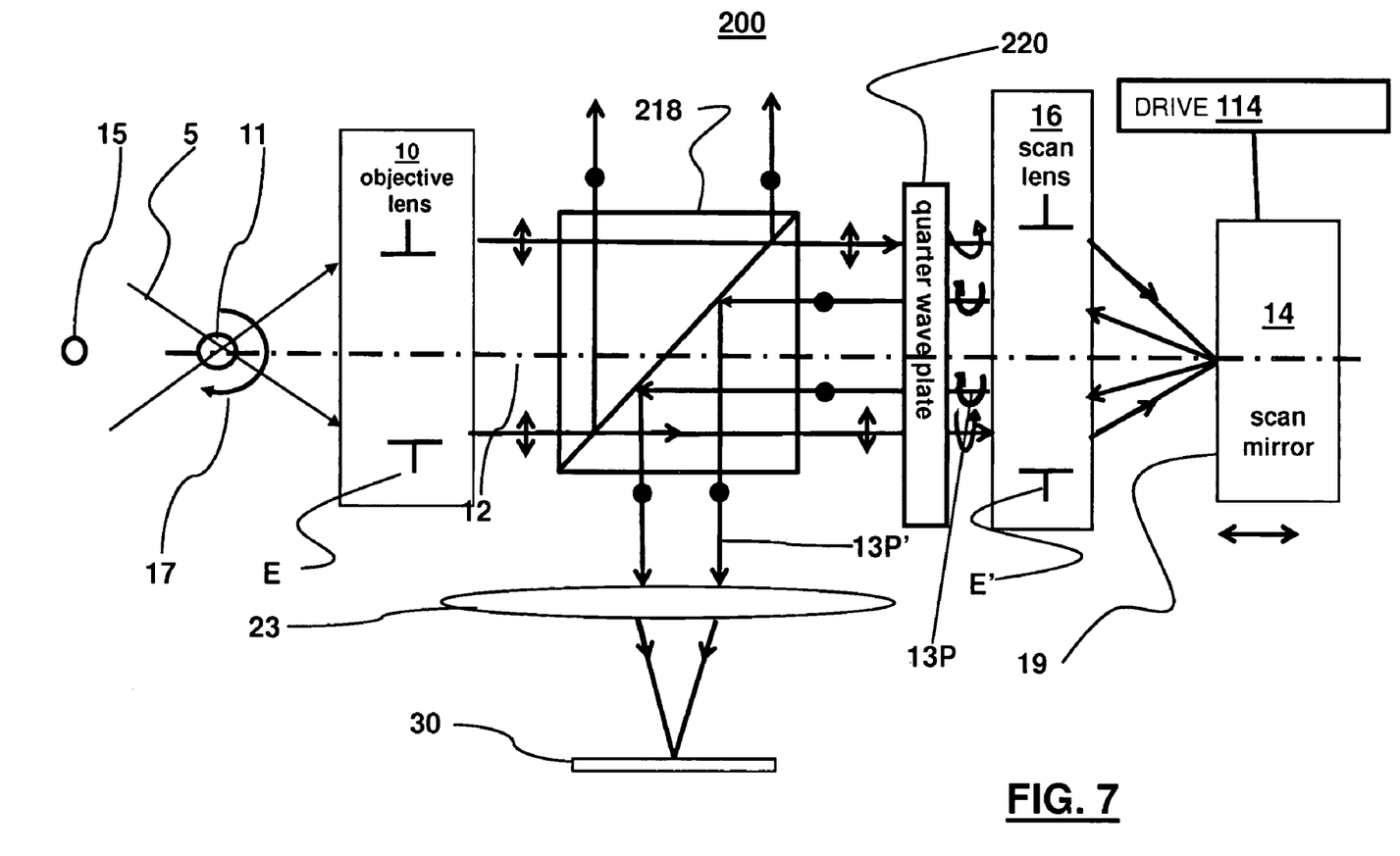
FIG. 7 schematically shows another example of a design for an optical tomography image acquisition system incorporating a quarter wave plate.

Referring now to FIG. 7, an example of an alternate design for an optical tomography system with a fast mechanical scan mirror employing a scan mirror used in cooperation with a quarter wave plate is schematically shown. An alternate fast scan mirror design 200 employs a polarizing beam splitter 218 optical aligned with a quarter wave plate 220 so as to transmit substantially circularly polarized light. The reflected light 13P from the scan mirror is then substantially circularly polarized with opposite handedness. The quarter wave plate 220 converts this to linear polarization light 13P' substantially orthogonal to the incident light 5. The beam splitter 218 is configured for directing the linear polarization light 13P' from the scan mirror 14 through the tube lens 23, ultimately transmitted onto the light sensor 30 for acquiring images of the tube contents. The other elements are similar in type, configuration and construction to those as described above with reference to FIG. 1.

The invention has been described herein in considerable detail in order to comply with the Patent Statutes and to provide those skilled in the art with the information needed to apply the novel principles of the present invention, and to construct and use such exemplary and specialized components as are required. However, it is to be understood that the invention may be carried out by specifically different equipment, and devices, and that various modifications, both as to the equipment details and operating procedures, may be accomplished without departing from the true spirit and scope of the present invention.

What is claimed is:

1. An optical projection tomography system for imaging an object of interest, the optical projection tomography system comprising:
    an illumination source;
    a carrier for holding the object of interest, a portion of which is located within the region illuminated by the light source, wherein the object of interest has at least one feature of interest located within the carrier;
    a microscope objective lens located to receive light passing through the carrier, the microscope objective lens located on an optical path;
    a variable power element located along the optical path, wherein the variable power element includes:
        a beam splitter,
        a scan lens,
        a scan mirror having a reflective surface for receiving light transmitted through the scan lens, where the microscope objective lens, the beam splitter, the scan lens, and the scan mirror are aligned along the optical path, and
        a driver coupled to oscillate the scan mirror along the optical path such that the reflecting surface remains perpendicular to the optical path whereby the oscillating scan mirror scans through a plurality of focal planes in the carrier;
    a second lens for receiving and transmitting light emitted from the variable power element; and
    a light sensor located to receive light transmitted from the second lens element.

2. The system of claim 1 wherein the second lens includes a tube lens; and wherein the beam splitter is also arranged to direct reflected light from the scan mirror through the tube lens.

3. The system of claim 1, wherein the driver comprises a piezoelectric transducer.

4. The system of claim 1 wherein the scan mirror oscillates at a rate of at least 500 Hz.

5. The system of claim 1 wherein the scan mirror oscillates at a rate of at least 1000 Hz.

6. The system of claim 1 wherein oscillation of the scan mirror results in a proportionally longer depth extension of a pseudo-projection image sensed by the light sensor.

7. The system of claim 1 wherein the driver comprises a piezoelectric actuator.

8. The system of claim 1 wherein the scan mirror and driver comprise a micro-electro-mechanical-systems flexure with a reflective coating.

9. The system of claim 1 wherein the scan mirror and driver comprise a metal mirror with a solenoid actuator.

10. The system of claim 1 wherein the driver comprises an acoustic wave generator driving a reflective elastic diaphragm.

11. The system of claim 1 wherein the carrier comprises an optically transparent capillary tube.

12. The system of claim 1 wherein the carrier is coupled to a rotational motor.

13. The system of claim 1 wherein the object is moved relatively to the light sensor to present multiple views for producing at least one image of the at least one feature of interest at each view.

14. The system of claim 1 wherein the object of interest comprises a biological cell.

15. The system of claim 1 wherein the light sensor comprises a detector selected from the group consisting of charge coupled devices, complementary metal-oxide-semiconductor devices, solid-state image sensors, and solid-state image sensor detector arrays.

16. The system of claim 1, wherein the carrier comprises an optically transparent capillary tube with a diameter of at least 50 microns.

17. The system of claim 1 wherein the scan lens has a numerical aperture (NA) value and an entrance pupil, and the microscope objective lens has an exit pupil, the system further comprising:
    an optical relay positioned to image the microscope objective lens exit pupil onto the scan lens entrance pupil; and
    where the microscope objective lens has an NA value that matches the scan lens NA value divided by the transverse magnification value (mT) between the object and the scan mirror.

18. The system of claim 1 wherein the microscope objective lens includes an exit pupil E and the variable power element (VPE) has a VPE entrance pupil E' comprises a beamsplitter, a scan mirror and a scan lens having an entrance pupil which is coincident with the VPE entrance pupil, where the exit pupil E is focused to be coincident with the entrance pupil E' and the beamsplitter, the scan mirror and the scan lens are aligned along an optical path with the microscope objective lens, and wherein the scan mirror is controlled by a driver.

19. The system of claim 18 further comprising an optical relay between the microscope objective lens and the variable power element.

20. The system of claim 19 wherein translating the scan mirror a distance $\Delta z'$ produces a focus shift $\Delta z$ at the object equal to $2 \Delta z' n/(n' m_T^2)$, where n is the object space index of refraction, n' is the scanner space index of refraction, and $m_T$ is the transverse magnification between an object and the scan mirror.

21. The system of claim 1 wherein the scan lens has an NA at least equal to the microscope objective lens NA divided by the transverse magnification $m_T$ between the object and scan mirror.

22. The system of claim 21 wherein the scan lens comprises a telecentric lens.

23. An optical projection tomography method for imaging an object of interest, the optical projection tomography method comprising:
   illuminating at least part of the object of interest within the field of view of a microscope objective lens located to receive light passing through the object of interest;
   transmitting light through the microscope objective lens to impinge upon a variable power element;
   driving the variable power element with respect to the microscope objective lens to scan through multiple focal planes in the object of interest, wherein driving the variable power element includes oscillating a scan mirror with a reflecting surface along an optical path such that the reflecting surface remains perpendicular to the optical path, whereby the oscillating scan mirror scans through a plurality of focal planes in the carrier; and
   sensing light transmitted from the variable power element.

24. The method of claim 23 wherein the scan mirror oscillates at a rate of at least 500 Hz.

25. The method of claim 23 wherein the scan mirror oscillates at a rate of at least 1000 Hz.

26. The method of claim 23 wherein driving the variable power element comprises translating a scan mirror a distance $\Delta z'$ to produces a focus shift $\Delta z$ at the object equal to a value according to the mathematical formula $$2 \Delta z' n/(n' m_T^2),$$

where n is the object space index of refraction, n' is the scanner space index of refraction, $m_T$ is the transverse magnification between the object of interest and the scan mirror.

27. The method of claim 23 further comprising holding the object of interest in a carrier, and rotating the carrier.

28. The method of claim 23 further comprising moving the object of interest relatively to the light sensor to present multiple views.

29. The method of claim 23 wherein the object of interest comprises a biological cell.

30. The method of claim 23 wherein transmitting light comprises imaging a microscope objective lens exit pupil onto a scan lens entrance pupil.

* * * * *